United States Patent [19]

Finegold et al.

[11] Patent Number: 4,711,231

[45] Date of Patent: Dec. 8, 1987

[54] IMPLANTABLE PROSTHESIS SYSTEM

[75] Inventors: Aaron N. Finegold, 136 Beechwood La., Pittsburgh, Pa. 15206; Maurice E. Taylor, Monroeville, Pa.

[73] Assignee: Aaron N. Finegold, Pittsburgh, Pa.

[21] Appl. No.: 926,186

[22] Filed: Nov. 3, 1986

[51] Int. Cl.$^4$ ................................................ A61F 2/26
[52] U.S. Cl. ........................ 128/79; 128/DIG. 25; 417/412
[58] Field of Search ............... 128/79, DIG. 25; 417/412; 222/209; 604/212

[56] References Cited

U.S. PATENT DOCUMENTS

| | | | |
|---|---|---|---|
| 3,817,237 | 6/1974 | Budduc | 128/DIG. 25 |
| 3,853,122 | 12/1974 | Strauch et al. | 128/79 |
| 4,009,711 | 3/1977 | Uson | 128/79 |
| 4,127,118 | 11/1978 | Latorre | 128/79 |
| 4,201,202 | 5/1980 | Finney et al. | 128/79 |
| 4,224,934 | 9/1980 | Scott et al. | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,378,008 | 3/1983 | Osbon, Sr. | 128/79 |
| 4,378,792 | 4/1983 | Finney | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,404,968 | 9/1983 | Evans, Sr. | 128/79 |
| 4,407,275 | 10/1983 | Schroeder | 128/79 |
| 4,407,278 | 10/1983 | Burton et al. | 128/79 |
| 4,412,530 | 11/1983 | Burton | 128/1 |
| 4,424,807 | 1/1984 | Evans, Sr. | 128/79 |
| 4,441,491 | 4/1984 | Evans, Sr. | 128/79 |
| 4,449,520 | 5/1984 | Palomar et al. | 128/79 |
| 4,523,584 | 6/1985 | Yachia et al. | 128/79 |
| 4,537,183 | 8/1985 | Fogarty | 128/79 |
| 4,549,530 | 10/1985 | Finney | 128/1 |
| 4,550,719 | 11/1985 | Finney et al. | 128/79 |
| 4,550,720 | 11/1985 | Trick | 128/79 |
| 4,558,693 | 12/1985 | Lash et al. | 128/79 |
| 4,559,931 | 12/1985 | Fischell | 128/79 |
| 4,566,446 | 1/1986 | Fogarty | 128/79 |
| 4,572,168 | 2/1986 | Fischell | 128/79 |
| 4,574,791 | 3/1986 | Mitchener | 128/79 |
| 4,574,792 | 3/1986 | Trick | 128/79 |
| 4,584,994 | 4/1986 | Bamberger et al. | 128/79 |
| 4,589,405 | 5/1986 | Hemmeter | 128/79 |
| 4,590,927 | 5/1986 | Porter et al. | 128/79 |
| 4,664,100 | 5/1987 | Rudloff | 128/79 |

*Primary Examiner*—Robert P. Swiatek
*Assistant Examiner*—Cary E. Stone
*Attorney, Agent, or Firm*—Webb, Burden, Robinson & Webb

[57] ABSTRACT

A surgically implantable prosthesis system including at least one flexible inflatable member and an imperforate housing. A flexible combination reservoir and pump located within the housing for storing liquid when the inflatable member is deflated and for pumping liquid into the inflatable member and a flexible tube connecting the combination reservoir and pump and the inflatable member for the passage of a liquid between the combination reservoir and pump and the inflatable member. A rechargeable battery operates a reversible electric motor located within the housing operatively connected to the combination reservoir and pump to collapse the combination reservoir and pump to force liquid out of the combination reservoir and pump through the tube into the inflatable member and to expand the combination reservoir and pump to receive liquid from the inflatable member and a battery located within the housing to operate the motor. An electric circuit located within the housing connects the battery to the motor and a pair of switches located outside of the housing and connected in the electric circuit between the battery and the motor to control operation of the motor. An internal charging coil is included in the electric circuit within the housing to recharge the battery and an external charging is used to induce current in the internal charging coil.

20 Claims, 7 Drawing Figures

IMPLANTABLE PROSTHESIS SYSTEM

BACKGROUND OF THE INVENTION

1. Field of the Invention

The invention relates generally to an implantable prosthesis system and more particularly to an implantable pumping system for overcoming erectile impotence and for controlling incontinence in both males and females.

2. Description of the Prior Art

Elongated silicone rubber inflatable cylinders are presently implanted in the corpora cavernosa of the penis and are filled with a liquid when an erection is desired. These cylinders are connected by flexible tubing to a manually operated squeeze bulb pump which is implanted in the scrotum. A flexible tube also extends from the squeeze bulb pump to a reservoir implanted in the abdominal cavity, and the reservoir contains liquid which is pumped to the cylinders by manually squeezing the bulb. A valve is located adjacent the squeeze bulb pump to control the flow of liquid through the tubes so that the liquid flows out of the reservoir through the pump and into the cylinders when the pump is compressed and is drawn out of the cylinders back into the reservoir through the pump when the flaccid state of the penis is desired. Such devices are successful but are difficult and embarrasing to manipulate and may have complicated aftereffects. Examples of such systems are disclosed in U.S. Pat. Nos. 3,954,102; 4,537,183 and 4,566,446.

Another prior art system utilizes an implanted pump assembly wherein the pump is driven by an implanted electric motor which is operated by a hand held stator located outside of the body. The pump moves fluid between a reservoir and inflatable cylinders implanted in the penis through tubes. The system is difficult and embarrasing to use since the stator must be plugged into house current and manually placed adjacent the motor rotor in order to operate the pump and transfer the fluid. This system is disclosed in U.S. Pat. No. 4,584,994.

SUMMARY OF THE INVENTION

The invention is a system for pumping liquid from a reservoir through flexible tubing into an implanted prosthesis to readily provide a controllable penile erection or to control incontinence.

This system provides a means for producing a usable penile erection in a physiologic-like manner without visually obvious physical maneuvers to accomplish erection. Similarly, no strenuous or painful maneuvers are necessary to deflate the inflated prosthesis so that the penis can return to the flaccid state. The system is completely implanted so that all parts thereof are concealed and is easily and simply operated so that physical and emotional discomfort are avoided.

When the system is used to control incontinence, an inflatable flexible annulus is implanted around the urethra which acts as a clamp to prevent the flow of urine when it is inflated and permits the flow of urine when it is deflated.

The system includes a sealed housing which contains a combination reservoir and pump, a reversible electric motor to operate the pump, a rechargeable battery to supply current to the motor and an internal charging coil to recharge the battery. The operation of the motor is controlled by the depression of tactile switches which are implanted in opposite sides of the user's abdomen. One switch controls the operation of the motor in one direction to pump liquid from the reservoir into the prosthesis, and the other switch operates the motor in the opposite direction to expand the reservoir and permit liquid to flow from the filled prosthesis back into the reservoir. The reservoir is a flexible bladder, and therefore the system does not require valves to control the direction of flow of the liquid. The battery is rechargeable by the internal charging coil included in the electric circuit so that the system may be operated over a long period of time without the necessity of surgery to replace the battery. The liquid utilized in the system may be either a non-toxic silicone oil or an isotonic saline in the solution both of which are physiologically compatible with the body tissues and organs in the event that a leak should develop in the system. The liquids are also compatible with medical grade silicone rubber from which the tubing and prosthesis are made. The liquid may contain radiopaque fluid which enables visualization of the location of the prosthesis subsequent to implantation, and should a leak occur, its location can be readily determined.

Briefly stated, the invention involves the implantation of a self-contained system within a human male to replace the erectile function of the corpora cavernosa of the penis with two inflatable and collapsible flexible cylinders or to control incontinence in both males and females by means of an inflatable annular clamp. The system may be connected to cylinders already in place in an impotent male, or it can be connected with cylinders which are implanted at the time the rest of the system is implanted. The system includes an elastomer doughnut reservoir having either an elliptical or a cylindrical shape. The doughnut reservoir is compressed to pump liquid from it into the inflatable prosthesis and is expanded to permit liquid to pass from the prosthesis into the reservoir. The combination reservoir and pump eliminates valves and a manually actuated squeeze bulb pump.

The foregoing and other objects and advantages of the invention will be apparent from the drawings and description which follows wherein like reference characters refer to like parts throughout.

DESCRIPTION OF THE PREFERRED EMBODIMENTS

Figure 1:
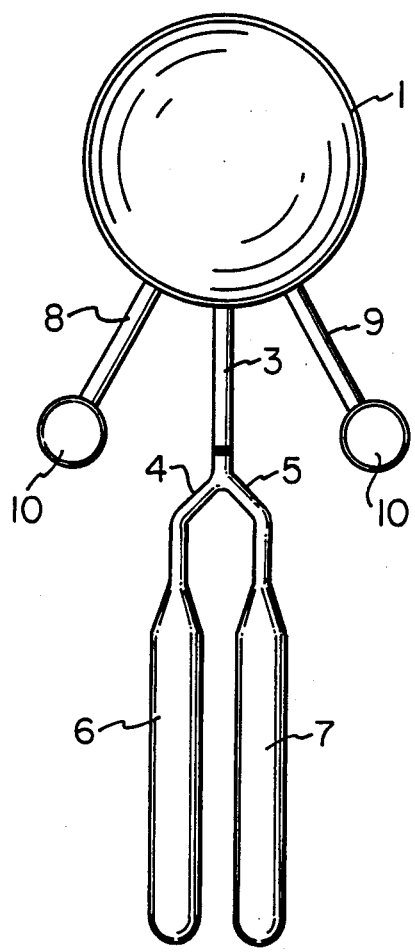
FIG. 1 is a plan view of an assembled system including a pair of flexible cylinders.

FIG. 1 shows a housing 1 which is a sealed unit and which may be made of a synthetic material such as a polyethylene which is biocompatible. A combination reservoir and pump 2 is located within housing 1. The combination reservoir and pump is connected to a kinkless synthetic biocompatible flexible inlet and outlet tube 3 which is connected to a flexible Y connector having legs 4 and 5 which may be connected to resilient medical grade silicone rubber cylinders 6 and 7 which are implanted in the corpora cavernosa of the penis. The cylinders are flexible and may be implanted in the penis either before or after connection to the legs 4 and 5 of the Y connector. That is, they may have been originally connected to a squeeze bulb pump such as shown, for example, in U.S. Pat. Nos. 4,566,446; 3,954,102 and 4,537,183 which will be replaced by the combination reservoir and pump of the invention.

A pair of biocompatible synthetic flexible tubes 8 and 9 are attached in sealed relationship to housing 1, and each tube is sealed to a synthetic biocompatible envelope 10 surrounding a tactile switch 11. The switches 11 and the envelopes 10 are identical and will be implanted on opposite sides of the abdomen. The switches are electrically connected with a reversible electric motor 15 and a battery 16 by wires passing through tubes 8 and 9. The switches reverse the polarity of electric motor 15 to reverse the direction of rotation of the gear drive for the combination reservoir and pump 2 for inflation and deflation of elongated cylinders 6 and 7. The switches are retained in the depressed position to maintain operation of the electric motor until the proper amount of liquid is forced out of the reservoir or is permitted to return to the reservoir.

Figure 2:
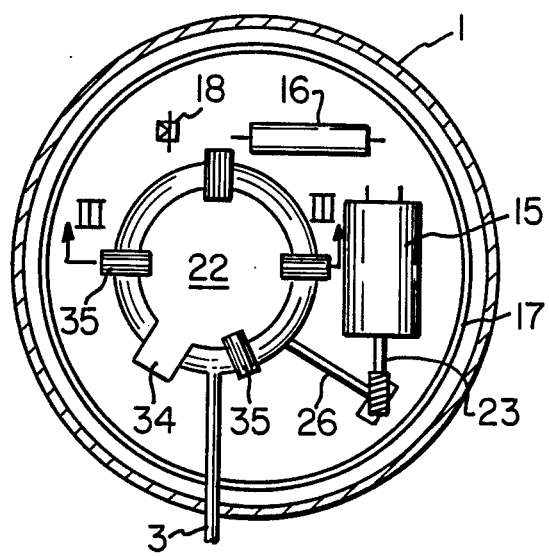
FIG. 2 is a horizontal section through the housing with the electric wiring omitted.
Figure 3:
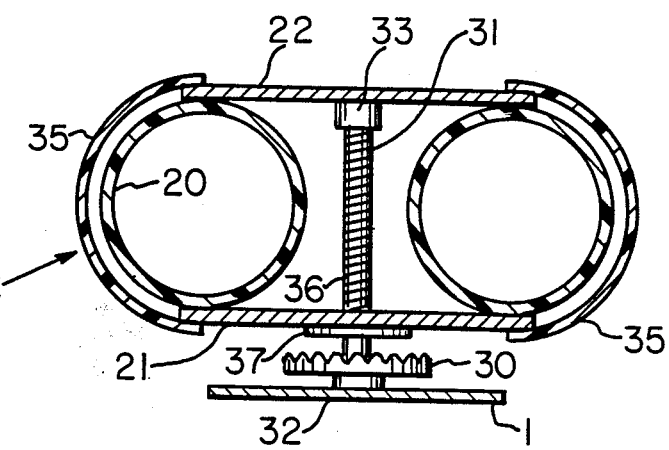
FIG. 3 is a vertical section through the combination reservoir and pump on line III—III of FIG. 2.
Figure 4:
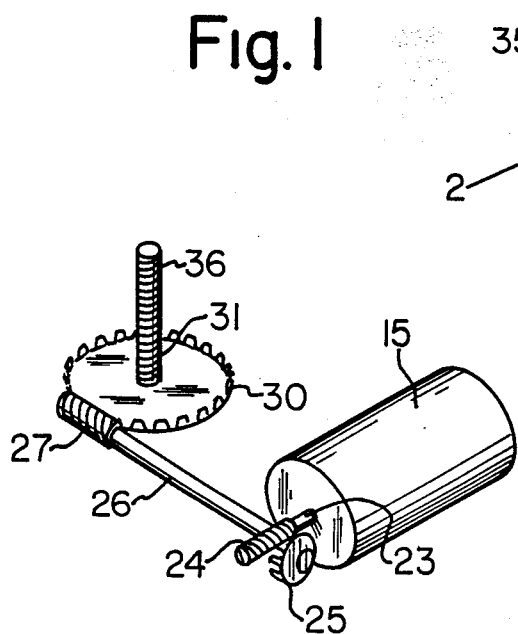
FIG. 4 is a perspective view of the electric motor and the pump drive.
Figure 5:
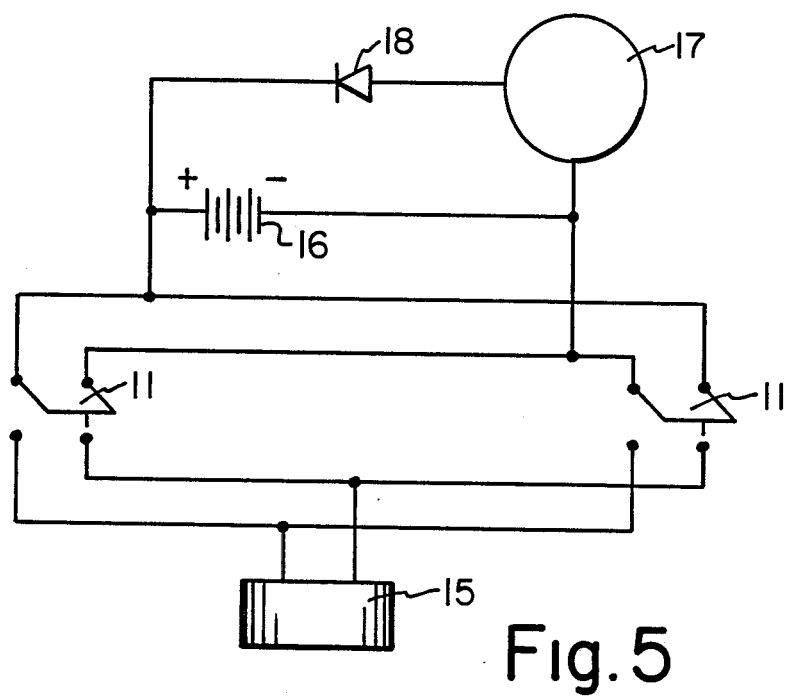
FIG. 5 is a circuit diagram including the electric motor, battery, switches and internal charging coil.

With specific reference to FIGS. 2, 3 and 4 of the drawings, it will be seen that housing 1 encloses reversible electric motor 15 which is electrically connected to a battery 16 and to an internal charging coil 17 having a diode 18 to prevent current flow from the battery to the coil. The electric motor 15 is reversible so that the mechanical drive arrangement operatively connecting motor 15 and combination reservoir and pump 2 may be reversed for transfer of liquid into and out of the combination reservoir and pump. The combination reservoir and pump 2 includes a flexible doughnut bladder 20 which is shown as having a cylindrical shape in FIG. 2 of the drawings, but it may also have an elliptical shape. The bladder 20 has a cylindrical cross section, as shown in FIG. 3, when it is filled with liquid. When the bladder is in the pumping mode, it is collapsed by movement of a piston plate 21 toward a stationary upper plate 22 as explained in more detail hereinafter.

The reversible motor 15 has a rotatable drive shaft 23 extending from one end thereof with a worm gear 24 formed on its free end. The worm gear 24 drives a pinion gear 25 which is fixed on the end of a shaft 26 mounted on the housing to rotate the shaft in either a clockwise direction or a counterclockwise direction depending upon the direction of rotation of worm gear 24 on drive shaft 23. The shaft 26 is mounted in bearings (not shown) fixed to the inner surface of the bottom of housing 1. The end of shaft 26 opposite the end carrying pinion gear 25 is formed with a worm gear 27 which drives a crown gear 30 which is fixed to a rotatable screw 31 mounted in a lower bearing 32 fixed to the upper surface of the bottom of housing 1 and an upper bearing 33 which is fixed to the lower surface of top plate 22. The stationary top plate 22 is supported by a depending leg 34 having its lower end fixed to the upper surface of the bottom of the housing. The flexible doughnut bladder 20 is attached to the facing surfaces of lower piston plate 21 and top plate 22. A plurality of flexible coupling members 35 are connected to piston plate 21 and stationary top plate 22. The screw 31 is formed with threads 36 throughout most of its length, and a threaded washer 37 located below and in contact with piston plate 21 is carried on threads 36 so that the washer and the piston plate move upwardly and downwardly along screw 31 depending upon the direction of rotation of screw 31. The movement of piston plate 21 relative to top plate 22 collapses doughnut bladder 30 or permits its expansion depending upon the direction of movement of screw 36. The coupling members 35 (four are shown in FIG. 2) are flexible and are attached to the top plate 22 and the piston plate 21 so that they collapse and expand with the movement of the piston plate depending upon the direction of rotation of the screw 31 as determined by the direction of rotation of the drive shaft 23 of motor 15.

The system shown in FIGS. 1–5 of the drawings operates in the following manner. When the flexible doughnut bladder 20 is compressed by upward movement of piston plate 21, liquid is forced out of the bladder through tube 3 into branches 4 and 5 of the Y connector and into flexible cylinders 6 and 7 to inflate the cylinders and create the erect penile condition. Alternatively, when piston plate 21 is permitted to move downwardly by rotation of screw 31, the liquid is forced out of cylinders 6 and 7 through the branches of the Y connector and tube 3 into the flexible bladder because the flexibility of cylinders 6 and 7 is greater than that of bladder 20. It is apparent that the system operates without the need of valving or a manual pump and thereby eliminates malfunctions which are caused by failure of these items.

Figure 7:
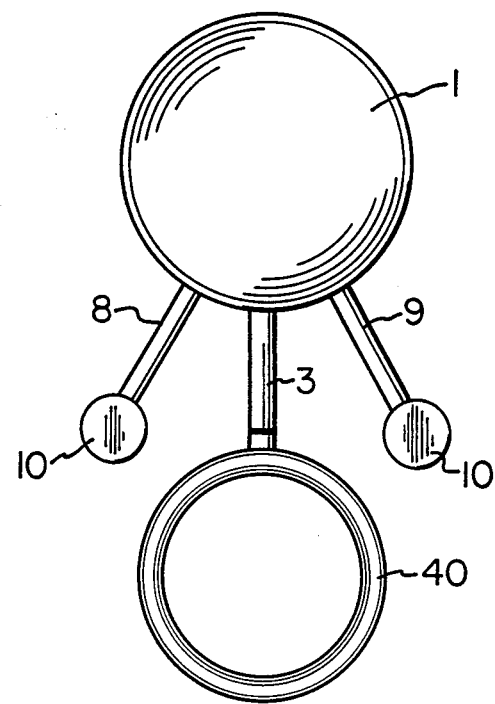
FIG. 7 is a plan view of a system for controlling incontinence.

FIG. 7 of the drawings shows a modification of the invention to control incontinence wherein the tube 3 from doughnut bladder 20 is connected to a flexible annulus 40. Annulus 40 is placed around the urethra to collapse the urethra and prevent urine discharge due to incontinence. In this system, expansion of annulus 40 causes it to close the urethra and prevent urine discharge, and deflation of the annulus permits urine discharge. Thus, it will be seen that annulus 40 acts as a clamp to control urine discharge. The housing 1 and the other elements of the modification shown in FIG. 7 of the drawings are identical with the modification shown in FIGS. 1–5 of the drawings except the Y connector is eliminated, and operation is controlled by depressing tactile switches 11 in envelopes 10.

Figure 6:
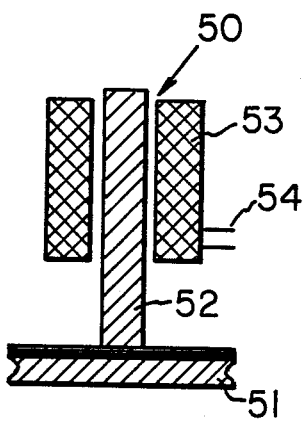
FIG. 6 is a vertical section with parts broken away of a portable external charger for charging the internal charging coil.

FIG. 6 of the drawings shows an external charger 50 for inducing a current in internal charging coil 17 to charge the rechargeable battery 16 in housing 1 in order to provide longer life for the battery and thereby eliminate frequent surgical procedures to replace the battery. The charger 50 shown in FIG. 6 consists of a casing 51, of which only a portion of the bottom wall is shown, having a core 52 attached thereto. The core 52 is formed of a low reluctance material such as ferrite. The core 52 is surrounded by an external charging coil 53 which is adapted to be attached to an alternating current source, such as regular house current having 120 volts and 60 cycles, by wires 54. When it is desired to recharge battery 16, the charger 50 is plugged into a house current outlet, and the upper end thereof is held close to the skin of the user near the center of internal charging coil 17 and is activated by a switch (not shown) in wires 54. The changing magnetic field created by external charger 50 passes through internal charging coil 17 to induce an electric current which charges battery 16. The coil may be held on the user's body by elastic straps, or it may be built into a cushion and placed upon the user's body adjacent the location of housing 1.

Depending upon the distance of internal charging coil 17 from the surface of the skin, it may be necessary to increase the peak power supplied to coil 17 from charger 50. This can be accomplished with a reasonable power input by decreasing the duty cycle of the signal supplied to external charging coil 53 of the charger 50. As an example, 120 volt, 60 cycle house current can be passed through a standard converter to produce an output signal having a series of constant voltage pulses which are spaced apart from each other and are supplied to external charging coil 53. The duty cycle is the ratio of the time the converter produces an output pulse to the time the converter is on. The voltage level of the constant voltage pulses can be much greater than the 120 volt peak level of house current. The duty cycle and the voltage level can be selected in a manner well known to those skilled in the art to induce a particular peak power and total power in internal charging coil 17.

While preferred embodiments of the invention have been described herein, it is to be understood that the invention may be embodied within the scope of the appended claims.

We claim:

1. A surgically implantable prosthesis system including at least one flexible inflatable member, an imperforate housing, a flexible combination reservoir and pump means located within said housing for storing liquid when said inflatable member is deflated and for pumping liquid into said inflatable member to inflate said inflatable member, a flexible connecting means extending out of said housing from said combination reservoir and pump means to said inflatable member for permitting the passage of liquid between said combination reservoir and pump means and said inflatable member, a battery operated power means located within said housing, drive means located within said housing operatively connecting said power means to said combination reservoir and pump means to collapse said combination reservoir and pump means to force liquid out of said combination reservoir and pump means through said connecting means into said inflatable member and to expand said combination reservoir and pump means to receive liquid from said inflatable member, a battery located within said housing, an electric circuit located within said housing connecting said battery to said power means and a pair of switches located outside of said housing and connected in said electric circuit between said battery and said power means to operate said power means, whereby closing one of said switches operates said power means and said drive means to collapse said combination reservoir and pump means to force liquid out of said combination reservoir and pump means into said inflatable member and closing the other of said switches operates said power means and said drive means to expand said combination reservoir and pump means so that liquid flows from said inflatable member into said combination reservoir and pump means.

2. A system as set forth in claim 1 wherein said power means is a reversible electric motor.

3. A system as set forth in claim 1 wherein said inflatable member is a hollow annulus adapted to surround the urethra and clamp it closed to control incontinence.

4. A system as set forth in claim 1 including a second inflatable member connected to said connecting means, said inflatable members are hollow tubes adapted to be implanted in the corpora cavernosa of the penis to control erection thereof.

5. A system as set forth in claim 1 wherein said power means includes a rotary drive shaft having a free end formed as a worm gear, said drive means including a rotary shaft mounted within said housing and having a pinion gear mounted on one end and a worm gear formed on the other end, said pinion gear meshing with said worm gear on said rotary drive shaft of said power means to rotate said rotary shaft and said worm gear formed on the other end said rotary shaft, a rotatable screw mounted on said housing and a crown gear fixed to the lower end of said screw, said crown gear meshing with said worm gear formed on the other end of said rotary shaft so that rotation of said rotary shaft rotates said crown gear and said screw and means movable along said screw to collapse and expand said flexible combination reservoir and pump means.

6. A system as set forth in claim 1 wherein said electric switches are implantable tactile switches.

7. A system as set forth in claim 1 including an internal charging coil located within said housing and electrically connected to said battery in said circuit, whereby said battery can be charged by an external charger without surgically removing said housing.

8. A system as set forth in claim 1 wherein said combination reservoir and pump means is an annular bladder attached to a stationary upper plate supported by said housing and to a movable lower piston plate and means for moving said piston plate relative to said stationary plate, whereby upward movement of said piston plate toward said stationary plate collapses said bladder to force liquid out of said bladder and downward movement of said piston plate away from said stationary plate expands said bladder so that liquid can flow into said bladder.

9. A system as set forth in claim 8 wherein said combination reservoir and pump means includes a plurality of flexible coupling members attached to the periphery of said upper plate and the periphery of said lower plate.

10. A system as set forth in claim 8 wherein said means for moving said piston plate is a rotatable threaded shaft extending between said stationary upper plate and the inner surface of the bottom of said housing and extending through an aperture in said piston plate to permit movement of said piston plate along said threaded shaft and a threaded washer mounted on said rotatable threaded shaft below and in contact with said piston plate, whereby rotation of said shaft by said drive means moves said threaded washer and said piston plate along said threaded shaft to control the internal volume of said bladder.

11. Apparatus for controlling the flow of a liquid, said apparatus comprising a housing, a flexible combination reservoir and pump means located within said housing for storing a liquid and for pumping liquid, a connecting means extending out of said housing from said combination reservoir and pump means for permitting the passage of liquid to and from said combination reservoir and pump means, a battery operated power means located within said housing, drive means located within said housing operatively connecting said power means to said combination reservoir and pump means to collapse said combination reservoir and pump means to force liquid out of said combination reservoir and pump means through said connecting means and to permit expansion of said combination reservoir and pump means to receive liquid from said connecting means, a battery located within said housing, an electric circuit located within said housing connecting said battery to said power means and a pair of switches located outside of said housing and connected in said electric circuit between said battery and said power means to operate said power means, whereby closing one of said switches operates said power means and said drive means to collapse said combination reservoir and pump means to force liquid out of said combination reservoir and pump means and closing the other of said switches operates said power means and said drive means to expand said combination reservoir and pump means to receive liquid.

12. Apparatus as set forth in claim 11 wherein said power means is a reversible electric motor.

13. Apparatus as set forth in claim 11 wherein said power means includes a rotary drive shaft having a free end formed as a worm gear, said drive means including a rotary shaft mounted within said housing and having a pinion gear mounted on one end and a worm gear formed on the other end, said pinion gear meshing with said worm gear on said rotary drive shaft to rotate said rotary shaft and said worm gear formed on the other end of said rotary shaft, a rotatable screw mounted on said housing and a crown gear fixed to the lower end of said screw, said crown gear meshing with said worm gear formed on the other end of said rotary shaft so that rotation of said rotary shaft rotates said crown gear and said screw and means movable along said screw to collapse said combination reservoir and pump means to force liquid out of said combination reservoir and pump means.

14. Apparatus as set forth in claim 11 wherein said electric switches are tactile switches.

15. Apparatus as set forth in claim 11 including an internal charging coil located within said housing and electrically connected to said battery in said circuit, whereby said battery can be charged by an external charger without being removed from said housing.

16. Apparatus as set forth in claim 11 wherein said combination reservoir and pump means is an annular bladder attached to a stationary upper plate supported by said housing and to a movable lower piston plate and means for moving said piston plate relative to said stationary plate, whereby upward movement of said piston plate toward said stationary plate collapses said bladder to force liquid out of said bladder and downward movement of said piston plate away from said stationary plate expands said bladder so that liquid can flow into said bladder.

17. Apparatus as set forth in claim 16 wherein said combination reservoir and pump means includes a plurality of flexible coupling members attached to the periphery of said upper plate and the periphery of said lower plate.

18. Apparatus as set forth in claim 16 wherein said means for moving said piston plate is a rotatable threaded shaft extending between said stationary upper plate and the inner surface of the bottom of said housing and extending through an aperture in said piston plate to permit movement of said piston plate along said threaded shaft and a threaded washer mounted on said rotatable threaded shaft below and in contact with said piston plate, whereby rotation of said shaft by said means moves said threaded washer and said piston plate along said threaded shaft to control the internal volume of said bladder.

19. In a surgically implantable prosthesis system including at least one flexible inflatable member and a flexible tube connected to said inflatable member for transferring a liquid to and from said inflatable member, the improvement comprising: an implantable imperforate housing, a combination reservoir and pump means located within said housing for storing liquid when said inflatable member is deflated and for pumping liquid into said inflatable member to inflate said inflatable member, said flexible tube extending into said housing and connected to said combination reservoir and pump means to permit the passage of liquid between said combination reservoir and pump means and said inflatable member, a battery operated reversible electric motor located within said housing, drive means located within said housing operatively connecting said electric motor to said combination reservoir and pump means to collapse said combination reservoir and pump means to force liquid out of said combination reservoir and pump means through said flexible tube into said inflatable member and to expand said combination reservoir and pump means to receive liquid from said inflatable member, a battery located within said housing, an electric circuit located within said housing connecting said battery to said electric motor and a pair of tactile switches located outside of said housing and connected in said electric circuit between said battery and said motor to operate said motor, whereby closing one of said switches operates said electric motor in one direction to activate said drive means to collapse said combination reservoir and pump means to force liquid out of said combination reservoir and pump means into said inflatable member and closing the other of said switches operates said electric motor in the opposite direction to activate said drive means to expand said combination reservoir and pump means so that liquid flows from said inflatable member into said combination reservoir and pump means.

20. In the system set forth in claim 19 wherein said electric motor has a rotary drive shaft having a free end formed as a worm gear, said drive means includes a rotary shaft in said housing and having a pinion gear mounted on one end and a worm gear formed on the other end, said pinion gear meshing with said worm gear on said rotary drive shaft of said electric motor to rotate said rotary shaft and said worm gear on the other end of said rotary shaft, a rotatable screw mounted in a bearing supported on said housing, a crown gear fixed to the lower end of said screw and meshing with said worm gear on the other end of said rotary shaft so that rotation of said rotary shaft rotates said crown gear and said screw and means movable along said screw to collapse said flexible combination reservoir and pump means to force liquid out of said combination reservoir and pump means and to expand said flexible combination reservoir and pump means to permit liquid to flow into said combination reservoir and pump means.

* * * * *